United States Patent [19]
Blackwood et al.

[11] Patent Number: 5,166,079
[45] Date of Patent: Nov. 24, 1992

[54] ANALYTICAL ASSAY METHOD

[75] Inventors: John J. Blackwood, Foxboro; Shai Inbar, Boston; Donna R. Maretsky, Reading, all of Mass.

[73] Assignee: PB Diagnostic Systems, Inc., Westwood, Mass.

[21] Appl. No.: 382,555

[22] Filed: Jul. 19, 1989

[51] Int. Cl.⁵ ............................................. G01N 33/533
[52] U.S. Cl. ..................................... 436/546; 435/7.1; 435/970; 436/8; 436/517; 436/518; 436/536; 436/800
[58] Field of Search ............... 435/805, 970; 436/518, 436/810, 8, 536, 546

[56] References Cited

U.S. PATENT DOCUMENTS

| | | | |
|---|---|---|---|
| 4,457,893 | 7/1984 | Takehawa | 422/64 |
| 4,459,358 | 7/1984 | Berke | 436/170 |
| 4,832,488 | 5/1989 | Hirai et al. | 356/243 |

FOREIGN PATENT DOCUMENTS

| | | |
|---|---|---|
| 0097952 | 1/1984 | European Pat. Off. . |
| 0278149 | 8/1988 | European Pat. Off. . |
| 0305563 | 3/1989 | European Pat. Off. . |
| 0370417 | 5/1990 | European Pat. Off. . |
| 8700023 | 1/1987 | PCT Int'l Appl. . |
| 2052057 | 1/1981 | United Kingdom . |

*Primary Examiner*—Sam Rosen
*Attorney, Agent, or Firm*—Gaetano D. Maccarone

[57] ABSTRACT

A method for determining the amount of an analyte in a sample fluid utilizes a multilayer assay element which comprises at least one reagent layer and a light-blocking layer. The assay method includes the steps of optically reading a signal producing species, e.g. a fluorescent label, a first time before the sample fluid is applied to the assay element and a second time, at the same wavelength and in the same location within the assay element, after the sample fluid has been applied to the assay element and the sample analyte has interacted with the reagent(s) present in the assay element. The ratio of the two signals is taken and compared with that for known amounts of the analyte to determine the amount of analyte in the sample fluid.

7 Claims, 1 Drawing Sheet

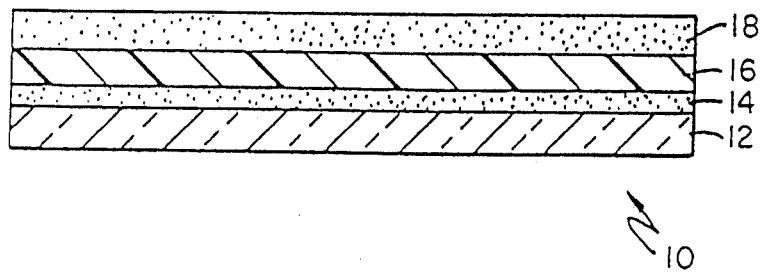

ANALYTICAL ASSAY METHOD

BACKGROUND OF THE INVENTION

The present invention relates to assays for the determination of analytes in fluids.

Many types of assay elements for the rapid analysis of analytes present in biological fluids are known in the art. Of particular interest are dry multilayer analytical elements to which the sample, e.g., a drop of blood, serum or plasma, is applied and allowed to migrate or diffuse to a reagent layer or layers. As a result of the interaction between the analyte and the reagent(s) present, a detectable change is brought about in the element corresponding to the presence of the analyte in the sample. The detectable change can be a color change which may be evaluated visually or read spectrophotometrically such as with a densitometer. In another scheme based on the presence of fluorescent-labeled biologically active species, a fluorescent output signal can be generated and read spectrofluorometrically. Such assay elements are of great interest because they can be adapted for use in automated analytical instruments.

In the automated analytical instruments a sample of a test fluid is typically provided in a sample cup and all of the assay method steps including pipetting of a measured volume of the sample onto an assay element, incubation and readout of the signal obtained as a result of the interactions(s) between the reagent(s) and the sample analyte are carried out automatically. The assay element is typically transported from one station, e.g. the pipetting station, to another, e.g. the optical read station, by a transport means such as a rotating carousel to enable the test steps to be carried out automatically.

Such automated analytical instruments are capable of processing many assay elements rapidly and it is necessary to achieve a very high level of precision for these assays. However, imprecisions in the results obtained can be caused by a number of factors. For example, any element to element variation in the distance from the optical readout apparatus to the signal-generating species when readout of the signal is carried out will introduce imprecision into the results as will any element to element variation in the thickness of the layer in which the signal-generating species resides when it is read.

The reagent layer(s) in thin film multilayer assay elements may be extremely thin, that is, on the order of about 0.01 mm or less. Accordingly, although such layers can be coated with a very high degree of precision nevertheless some slight variation in the thickness of the reagent layers will exist on an element to element basis. Similarly, although the transport means e.g. a carousel, for the assay elements can be engineered within very exact tolerances, nevertheless there will exist some slight variations in the instrument position response for the respective assay element positions on the transport means.

It is desirable therefore to have a method for compensating for signal imprecisions caused by variations in reagent levels from element to element and variations in instrument position response as well those caused by other factors.

BRIEF SUMMARY OF THE INVENTION

These and other objects and advantages are accomplished in accordance with the invention by providing a method for determining the amount of an analyte in a sample fluid such as whole blood, plasma, serum, etc. The assay method is carried out with an assay element which includes at least one reagent layer and a light-blocking layer. The light-blocking layer provides an optical bound/free separation of a signal-generating species as a function of the amount of analyte in the sample fluid. The signal-generating species in the assay element is read optically a first time prior to delivering the sample fluid to the element. Subsequently, after the sample fluid has been applied to the assay element and the interaction between the sample analyte and the reagent(s) present in the element has taken place, the signal producing species is read optically a second time. This second optical reading is carried out by irradiating the same layer of the assay element as that read in the first optical reading and doing so at the same wavelength. The ratio of the second signal to the first signal is taken and compared with that for known amounts of the analyte to determine the amount of the analyte in the sample fluid.

By normalizing the signal obtained from the assay in this manner it is possible to compensate for variations in reagent levels because of variations in reagent layer thicknesses from element to element and also for variations in the analytical instrument position response. The compensation for such variations provides significantly improved precision in the assay method.

BRIEF DESCRIPTION OF THE DRAWINGS

For a better understanding of the invention as well as other objects and further features thereof, reference is made to the following detailed description of various preferred embodiments thereof taken in conjunction with the accompanying drawings wherein: the Figure is a partially schematic cross-sectional view of an assay element which can be utilized in the method of the invention.

DESCRIPTION OF THE PREFERRED EMBODIMENTS

The assay elements which are utilized in the assay method of the invention may include any suitable signal-generating species. Any light radiation emitting or absorbing label, including a label which reacts with a reagent, which provides a detectable signal can be utilized as the signal-generating species. The label may be a fluorophore, a phosphor or a light absorbing material.

The assay method of the invention will be described in detail with respect to a preferred embodiment of an assay element which may be utilized therein. Referring now to the Figure there is seen an assay element 10 which is a thin film multilayer element typically having a thickness of about 0.1 mm and comprised of a transparent support 12 which carries in succession a reagent layer 14, a light-blocking layer 16 and an optional top coat layer 18 which may serve as a reagent layer, a filter layer such as for proteins, an anti-abrasion layer, etc. The reagent layer 14 is very thin, typically having a thickness of about 0.025 mm and includes an immunocomplex of a binding partner for the analyte of interest and a conjugate of a labeled analyte (the same as the sample analyte, an analogue thereof or a structurally similar material which will bind to the binding partner). The binding partner, an antibody when the sample analyte is an antigen, is immobilized in the reagent layer 14 by being covalently bound to the surface of the support layer 12, which may be of any appropriate material such as a polyester or a polystyrene, or to a matrix material or by being physically held by the matrix material. The matrix material may be a hydrophilic gel material such as gelatin, a polysaccharide, e.g. agarose, a derivatized polysaccharide, mixtures thereof, and the like. Light-blocking layer 16 may comprise any suitable material such as, for example, iron oxide, titanium dioxide or the like dispersed in a binder material such as a polysaccharide. The optional topcoat layer 18 may comprise an anti-abrasion layer of a material such as a polysaccharide or preferably may include buffers, blocking and displacing agents, etc.

The assay element 10 may also include a layer or other means (not shown) for distributing the sample fluid uniformly across the surface of the top layer of the element. Any suitable fluid distribution technique may be used including, for example, particulate layers, polymeric layers, fibrous layers, woven fabric layers and liquid transport systems which have been disclosed in the art as being suitable for this purpose. Many such liquid distribution systems and materials for providing a uniform distribution of a fluid sample across the surface of an assay element are known in the art and therefore extensive discussion of such materials and systems is not required here. A particularly preferred fluid transport system is that described in commonly assigned, copending application Ser. No. 210,732, filed Jun. 23, 1988 now U.S. Pat. No. 5,051,237. The distribution means, whether a layer of fibrous material, etc. or a liquid transport system is preferably relatively thick in comparison to reagent layer 14.

In practice, the label which is present in reagent layer 14 is optically read prior to applying the sample to the assay element by irradiating layer 14 with the appropriate electromagnetic radiation through transparent support layer 12 to obtain a first readout signal. The sample fluid is then distributed across the surface of the assay element and the fluid diffuses throughout layers 14, 16 and 18 as well as any fluid distribution layer or liquid transport system present and an equilibrium is established. The analyte present in the sample will compete with the labeled analyte in reagent layer 14 for the available binding sites on the antibodies immobilized in layer 14, the labeled analyte being dissociated therefrom and replaced by the sample analyte in a ratio appropriately equal to the relative amounts of sample analyte and labeled analyte. Thus, depending upon the amount of analyte in the sample, some percentage of the labeled analyte initially bound to the immobilized antibodies in layer 14 will be displaced therefrom and distributed throughout the remainder of the assay element, The amount of labeled analyte bound to the immobilized antibodies in reagent layer 14 at any time is inversely proportional to the amount of sample analyte.

A second readout signal is obtained by again irradiating reagent layer 14 through support layer 12 with the same electromagnetic radiation used in the first optical read step to obtain a second signal which is inversely proportional to the amount of sample analyte, that is, the signal decreases as the amount of sample analyte increases. Since reagent layer 14 is relatively thin in comparison to the combined thickness of layers 16 and 18 together with that of any fluid distribution layer or liquid transport system present and because light blocking layer 16 prevents any of the readout electromagnetic radiation from entering layer 18 or anything above it, the second signal obtained will be a function of the labeled analyte which is bound to the immobilized antibodies and a small percentage of the free labeled analyte which is distributed throughout the remainder of the assay element. In a preferred embodiment the ratio of the thickness of reagent layer 14 to the combined thickness of the light-blocking layer and the remainder of the assay element is from about 1:20 to about 1:100 or more.

The ratio of the second signal to the first signal is taken and compared with that for known amounts of the analyte to determine the amount of analyte in the sample fluid. The ratio may be used as obtained or it may be multiplied by some constant, dependent upon the particular assay, to provide a signal which falls in some desired range.

In commercial use the assay is preferably carried out in an automated analytical instrument which performs the analysis automatically and records the result. By practicing the assay method of the invention variations in the instrument position response and in the thickness of the reagent layer from element to element can be compensated for and significantly better precision obtained.

The invention will now be described further in detail with respect to specific preferred embodiments by way of examples, it being understood that these are intended to be illustrative only and the invention is not limited to the materials, procedures, etc. recited therein.

EXAMPLE I

An assay element was prepared comprising a transparent polyethylene terephthalate support having coated thereon in succession:

1. a reagent layer comprising about 500 mg/m$^2$ of a 3:1 mixture of agarose and glyoxyl agarose; about 72 mg/m$^2$ of bis tris propane buffer; about 10 mg/m$^2$ of an antibody raised against theophylline; and about 0.07 mg/m$^2$ of a fluorescent labeled theophylline conjugate represented by the formula

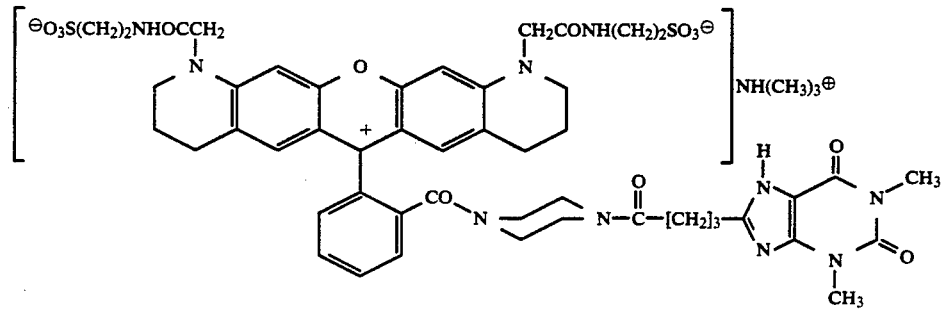

2. a light-blocking layer comprising about 6000 mg/m² of iron oxide, about 2000 mg/m² of agarose and about 50.4 mg/m² of 2'-morpholino ethane sulfonic acid (pH 5.7); and 3. a topcoat layer comprising about 2000 mg/m² of agarose.

Test samples containing different levels of theophylline in a buffer solution were prepared. The buffer solution was made up of 50 mM of hydroxyethyl piperazine ethyl sulfonate (HEPES) buffer, pH 7.2, 150 mM of sodium chloride, 10 mM of EDTA and 1% of Polygeline. Each sample was run in quadruplicate.

Each assay element was inserted into a laboratory analytical instrument and conditioned at 37° C. for about two minutes. The test element was then irradiated through the transparent support with 550 nm light and the fluorescent emission measured at 580 nm. The test sample, about 10 µl, was then applied to the assay element which was incubated for an additional six minutes and then read again. The data obtained are shown in Table I. Each value shown is the average of four readings from the four quadruplicates run for each test sample. The normalized signal value was obtained by taking the values obtained from dividing the wet reading by the dry reading and multiplying them by a constant which in this case was 1.166.

TABLE I

| THEOPHYLLINE (µg/dl) | DRY SIGNAL (V) | DRY CV (%) | WET SIGNAL (V) | WET CV (%) | NORMALIZED SIGNAL (V) | NORMALIZED CV (%) |
|---|---|---|---|---|---|---|
| 2.5 | 1.192 | 7.5 | 1.256 | 8.6 | 1.229 | 1.3 |
| 5.0 | 1.174 | 7.2 | 1.016 | 10.0 | 1.008 | 4.1 |
| 20.0 | 1.176 | 7.9 | 0.683 | 11.0 | 0.678 | 5.2 |
| 40.0 | 1.180 | 11.2 | 0.561 | 22.0 | 0.551 | 10.8 |

It is seen that normalizing the signal in accordance with the method of the invention provides significantly improved precision. Also, the data show that the improved precision was obtained at theophylline levels across the assay range (2.5–40.0 µg/dl).

EXAMPLE II

An assay element similar to that illustrated in Example I was prepared wherein the reagent layer included about 20 mg/m² of an antibody raised against phenytoin and about 0.15 mg/m² of a conjugate consisting of phenytoin bound to the fluorescent moiety illustrated in Example I.

Test samples containing 0, 5 and 40 µg/dl respectively of phenytoin were prepared in a buffer solution which was the same as that described in Example I with the exceptions that it contained about 2% BSA, about 0.01% NaN₃ and about 0.01% PNS and did not contain Polygeline.

The assay procedure was the same as that previously described. Eighteen assays were run for each concentration. The data obtained are shown in Table II. The normalized signal value was obtained by multiplying the ratio of the wet to dry readings by 3.836.

TABLE II

| PHENYTOIN (µg/dl) | DRY SIGNAL (V) | DRY CV (%) | WET SIGNAL (V) | WET CV (%) | NORMALIZED SIGNAL (V) | NORMALIZED CV (%) |
|---|---|---|---|---|---|---|
| 0 | 3.682 | 5.4 | 6.806 | 4.8 | 7.090 | 1.7 |
| 5 | 3.724 | 2.8 | 5.542 | 2.6 | 5.710 | 1.4 |
| 40 | 3.533 | 3.8 | 3.417 | 8.9 | 3.711 | 7.9 |

It can be seen that normalizing the signal according to the invention gave significantly improved precision.

EXAMPLE III

An assay element similar to that illustrated in Example I was prepared wherein the reagent layer included about 15 mg/m² of an antibody raised against phenobarbital and about 0.15 mg/m² of a conjugate consisting of phenobarbital bound to the fluorescent moiety illustrated in Example I.

Test samples containing 0 and 5 µg/dl, respectively, of phenobarbital in pooled human serum were prepared. The assay procedure was the same as that previously described. Three assays were carried out for each concentration. The results obtained are shown in Table III. The normalized signal value was obtained by multiplying the ratio of the wet to dry readings by 3.0.

TABLE III

| PHENO-BARBITAL (µg/dl) | DRY SIGNAL (V) | DRY CV (%) | WET SIGNAL (V) | WET CV (%) | NORMALIZED SIGNAL (V) | NORMALIZED CV (%) |
|---|---|---|---|---|---|---|
| 0 | 4.112 | 5.13 | 5.002 | 6.08 | 3.648 | 1.24 |
| 5 | 3.886 | 10.66 | 3.462 | 11.56 | 2.671 | 1.05 |

The results show that normalizing the signal according to the invention provided significantly improved precision.

EXAMPLE IV

An assay element similar to that illustrated in Example I was prepared wherein the reagent layer included about 0.5 mg/m² of an antibody raised against T4 and about 0.01 mg/m² of a conjugate consisting of T4 bound to the fluorescent moiety illustrated in Example I.

Test samples containing 0.0, 2.5 and 10.0 µg/dl, respectively, of T4 in plasma (stripped of T4) were prepared. The assay procedure was the same as that previously described. Twelve assays were carried out for each concentration. The results are shown in Table IV. The normalized signal value was obtained by multiplying the ratio of the wet to dry readings by 3.0.

TABLE IV

| T4 (μg/dl) | DRY SIGNAL (V) | DRY CV (%) | WET SIGNAL (V) | WET CV (%) | NORMALIZED SIGNAL (V) | NORMALIZED CV (%) |
|---|---|---|---|---|---|---|
| 0 | 2.573 | 3.85 | 2.735 | 3.67 | 3.190 | 1.40 |
| 2.5 | 2.552 | 4.80 | 2.522 | 5.00 | 2.965 | 1.52 |
| 10.0 | 2.512 | 4.42 | 1.907 | 5.97 | 2.276 | 2.14 |

The data show that significantly improved precision was obtained by normalizing the signal according to the invention.

Although the invention has been described with respect to specific preferred embodiments it is not intended to be limited thereto but rather those skilled in the art will recognize that variations and modification may be made therein which are within the spirit of the invention and the scope of the appended claims.

What is claimed is:

1. A method for determining the presence of an analyte in a sample fluid comprising
   (a) distributing a sample of fluid across the surface of a multilayer assay element which comprises:
      i. a light-blocking layer which is permeable to said fluid; and
      ii. a reagent layer comprising an immobilized specific binding partner for said analyte and a conjugate of a label bound to a moiety which binds to said binding partner, wherein said analyte and said specific binding partner are each a member of an antigen-antibody binding pair;
   (b) obtaining a readout signal after step (a) by irradiating said reagent layer with electromagnetic radiation which is in the absorption region of said label;
   (c) taking the ratio of said readout signal from step (b) to a readout signal obtained by irradiating said reagent layer with the same electromagnetic radiation used in step (b) prior to distributing said fluid sample in step (a); and
   (d) comparing said ratio with like ratios obtained for known concentrations of said analyte to determine the concentration of analyte in said sample.

2. The method as defined in claim 1 wherein said assay element further includes a support which is transparent to said electromagnetic radiation.

3. The method as defined in claim 2 wherein said moiety bound to said label is said analyte or an analogue thereof.

4. The method as defined in claim 2 wherein said label is fluorescent.

5. The method as defined in claim 2 wherein said assay element further includes a top layer arranged above said light blocking layer.

6. The method as defined in claim 2 wherein the ratio of the thickness of said reagent layer to that of the remainder of said assay element is from about 1:20 to about 1:100.

7. The method as defined in claim 2 wherein said analyte is an antigen and said specific binding partner is an antibody.

* * * * *